United States Patent
Shultz et al.

(10) Patent No.: US 6,273,089 B1
(45) Date of Patent: Aug. 14, 2001

(54) AUTOMATIC MECHANICAL LOCK DOWN FOR TRANSPORTABLE LIFE SUPPORT SYSTEM

(75) Inventors: Douglas Ellwood Shultz, Brea; James Richard Ausbourne, Torrance, both of CA (US)

(73) Assignee: Integrated Medical Systems, Inc., Signal Hill, CA (US)

( * ) Notice: Subject to any disclaimer, the term of this patent is extended or adjusted under 35 U.S.C. 154(b) by 0 days.

(21) Appl. No.: 09/285,935

(22) Filed: Apr. 2, 1999

Related U.S. Application Data

(63) Continuation-in-part of application No. 08/667,693, filed on Jun. 21, 1996, now Pat. No. 5,975,081.

(51) Int. Cl.$^7$ ................................................. A61G 15/00
(52) U.S. Cl. ........................ 128/845; 128/869; 24/601.5
(58) Field of Search ........................... 128/845, 869; 24/72.5, 601.5, 462; 5/424, 503.1, 658

(56) References Cited

U.S. PATENT DOCUMENTS

| | | |
|---|---|---|
| 1,200,852 | 10/1916 | Kern . |
| 1,258,694 | 3/1918 | Miller . |
| 1,287,855 | 12/1918 | Brand . |
| 1,754,959 * | 4/1930 | Matushenko ................. 24/601.5 |
| 2,704,989 | 3/1955 | Konecny ................................ 114/5 |
| 2,837,778 | 6/1958 | Kern ........................................ 20/2 |
| 3,050,331 | 8/1962 | Mansen ................................ 296/27 |
| 3,148,911 | 9/1964 | Boyer et al. ........................ 296/19 |
| 3,292,226 * | 12/1966 | Foster ................................ 24/601.5 |
| 3,376,059 | 4/1968 | Corl ...................................... 287/99 |
| 3,492,042 | 1/1970 | Nachtigall, Jr. ..................... 296/24 |
| 3,531,151 | 9/1970 | Branfield ............................. 296/23 |
| 3,761,968 | 10/1973 | Besler ..................................... 5/92 |
| 3,775,782 | 12/1973 | Rice et al. ............................. 5/82 |
| 3,840,265 | 10/1974 | Stirling et al. .................... 296/19 |
| 4,060,079 | 11/1977 | Reinhold, Jr. ................. 128/145.8 |
| 4,161,172 | 7/1979 | Pickering ................................ 128/1 |
| 4,224,936 | 9/1980 | Cox .................................... 128/132 |
| 4,352,991 | 10/1982 | Kaufman .............................. 307/9 |
| 4,425,978 | 1/1984 | Star ..................................... 180/243 |
| 4,584,989 | 4/1986 | Stith ........................................ 128/1 |

(List continued on next page.)

FOREIGN PATENT DOCUMENTS

| | | |
|---|---|---|
| AU9500477 | 2/1996 | (AU) . |
| 141669 | 12/1973 | (DE) . |
| 0343077 | 11/1989 | (EP) . |
| 1373384 | 11/1962 | (FR) . |
| 1473862 | 5/1977 | (GB) . |

OTHER PUBLICATIONS

Buchanan Aircraft Corporation Engineered Composites.
Spectrum Aeromed–Above and Beyond 1995.
Mobi–The Intensive Care Unit.
The Results of Innovative–Lifeport, Inc.
Mobile Intensive Care Rescue Facility (MIRF).
Aeromed Systems, Inc.—Specification/AMT 300.

*Primary Examiner*—Michael A. Brown
(74) *Attorney, Agent, or Firm*—Stetina Brunda Garred & Brucker

(57) ABSTRACT

An automatic mechanical lockdown for releasably attaching a litter to a transportable life support system has a base having a recess formed therein and a generally arcuate latch typically attached to the base. The recess of the base is sized to receive a pole of a litter. The latch has open and closed positions with respect to the recess such that the latch is pushed from the closed position thereof to the open position thereof when a litter pole is moved toward the recess of the base. The latch returns and remains in the closed position thereof when a litter pole is disposed within the recess. A spring which is attached to the base and the latch biases the latch in the closed position thereof. The latch can be moved from the closed position to the open position thereof by a person's thumb while the person maintains his grasp upon a litter pole.

2 Claims, 2 Drawing Sheets

U.S. PATENT DOCUMENTS

| | | | |
|---|---|---|---|
| 4,680,790 | 7/1987 | Packard et al. | 379/432 |
| 4,724,844 | 2/1988 | Rafelson | 128/670 |
| 4,747,172 | 5/1988 | Hohol et al. | 5/507 |
| 4,757,811 | 7/1988 | Clark | 129/134 |
| 4,768,241 | 9/1988 | Beney | 5/60 |
| 4,780,919 | 11/1988 | Harrison | 5/60 |
| 4,783,109 | 11/1988 | Bucalo | 296/20 |
| 4,957,121 | 9/1990 | Icenogle et al. | 128/897 |
| 5,005,230 | 4/1991 | Congdon | 5/60 |
| 5,016,307 | 5/1991 | Rebar | 5/503 |
| 5,034,181 | 7/1991 | Billiu | 264/517 |
| 5,050,254 | 9/1991 | Murphy | 5/82 |
| 5,077,843 | 1/1992 | Dale et al. | 5/60 |
| 5,084,922 | 2/1992 | Louit | 5/81.1 |
| 5,092,722 | 3/1992 | Reazer, III et al. | 410/104 |
| 5,111,818 | 5/1992 | Suzuki et al. | 128/644 |
| 5,117,521 | 6/1992 | Foster et al. | 5/510 |
| 5,121,514 | 6/1992 | Rosane | 5/628 |
| 5,173,142 | 12/1992 | Billiu | 156/245 |
| 5,229,052 | 7/1993 | Billiu | 264/115 |
| 5,236,390 | 8/1993 | Young | 454/95 |
| 5,271,128 * | 12/1993 | Storm | 24/601.5 |
| 5,306,026 | 4/1994 | Jesse | 280/18 |
| 5,335,651 | 8/1994 | Foster et al. | 128/202.13 |
| 5,338,588 | 8/1994 | Billiu | 428/36.3 |
| 5,342,121 | 8/1994 | Koria | 312/1 |
| 5,421,340 | 6/1995 | Stanga et al. | 128/671 |
| 5,433,222 * | 7/1995 | Boomgaarden | 128/876 |
| 5,494,051 | 2/1996 | Schneider, Sr. | 128/870 |
| 5,497,766 | 3/1996 | Foster et al. | 128/200.24 |
| 5,570,483 | 11/1996 | Williamson | 5/83.1 |
| 5,615,430 | 4/1997 | Nambu et al. | 5/600 |
| 5,626,151 | 5/1997 | Linden | 128/897 |
| 5,630,238 | 5/1997 | Weismiller et al. | 5/600 |
| 5,680,661 | 10/1997 | Foster et al. | 5/618 |
| 5,749,374 | 5/1998 | Schneider, Sr. | 128/870 |

\* cited by examiner

AUTOMATIC MECHANICAL LOCK DOWN FOR TRANSPORTABLE LIFE SUPPORT SYSTEM

RELATED APPLICATION

This patent application is a continuation-in-part patent application of U.S. Ser. No. 08/667,693, filed Jun. 21, 1996, now U.S. Pat. No. 5,975,081, and entitled SELF-CONTAINED TRANSPORTABLE LIFE SUPPORT SYSTEM, the contents of which are hereby incorporated by reference.

FIELD OF THE INVENTION

The present invention relates generally to transportable life support systems such as those utilized to treat intensive care patients when they are moved from one location to another. The present invention relates more particularly to an automatic mechanical lock down which is utilized to releasably attach the poles of a litter to the transportable life support system so that the patient can easily and rapidly be placed thereupon and be removed therefrom.

BACKGROUND OF THE INVENTION

It is frequently necessary to transport medical patients from the site of an accident or injury to a hospital. For example, persons suffering from various medical emergency conditions such as heart attacks, and strokes must be transported quickly to a medical facility. Medical personnel speak of a "golden hour" within which such a medical patient must be transported to a medical facility so that proper medical care can be provided therefor. The survival rate for such medical patients is greatly enhanced if they are transported to the medical facility within the golden hour.

As those skilled in the art will appreciate, it is frequently difficult to transport a patient to a remotely located medical facility in a timely manner, particularly within the desired golden hour. It is not unusual for accidents to occur at remote locations. Thus, a substantial amount of time may be required to transport the medical patient to a distant hospital. Also, in battlefield situations it is frequently impossible to transport a casualty immediately. In either instance, the patient may be located hundreds, if not thousands, of miles from a hospital, thus necessitating several hours of transport time. As such, it is frequently beneficial to perform various emergency medical procedures at the site of the medical problem, and to attempt to provide ongoing medical care during transport to a remote hospital. The mortality rate of such transported medical patients is substantially reduced.

It is well-known to use various different medical devices in the field, i.e., at locations remote from a medical facility, so as to enhance a medical patient's chance of survival. For example, it is well-known to use an electrocardiograph (ECG) and a defibrillator upon heart attack victims so as to monitor the condition thereof and so as to provide medical treatment therefor in field.

Typically, the medical patient is placed upon a litter and then various different medical devices are used upon the patient, as necessary. During transport the medical devices may either be temporarily disconnected from the patient, or alternatively may be hand carried along therewith by additional personnel. However, disconnection of the medical devices from the patient results in the undesirable disruption of medical monitoring and/or treatment therefor. Hand carrying the medical devices along with the patient requires extra personnel, which may not be available, or for which there may not be adequate room within the transport vehicle.

As such, it is desirable to provide a system for transporting a medical patient wherein the medical devices are carried along with the stretcher. In an attempt to provide such a system for transporting a medical patient while facilitating the continuous use of medical devices thereupon, the Mobile Intensive Care Rescue Facility (MIRF) was developed by the Royal Australian Army Medical Corp. the MIRF is intended to provide sufficient medical equipment to have the capabilities of an intensive care hospital ward. The MIRF is designated so as to facilitate the removal and replacement of the various pieces of medical equipment therefrom for maintenance. The MIRF is specifically designed to accommodate two major roles: the transfer of critically ill people from one point to another, such as from a ward to an x-ray room or from one hospital to another; and the bringing of life support systems quickly to the scene of an accident or other medical emergency.

The MIRF can be configured to include a blood pressure cuff, an invasive blood pressure monitor, a body temperature sensor, a heart rate sensor (finger clip sensor), an oxygen saturation sensor, an exhaled air carbon dioxide sensor, and an electrocardiograph, so as to facilitate medical monitoring of a patient. Further, the MIRF can include a ventilation system, a volumetric infusion pump, a syringe pump, a suction unit, and a defibrillator so as to facilitate medical treatment.

Another contemporary system is the MOBI described in U.S. Pat. No. 4,957,121, issued to Icenogle et al. on Sep. 18, 1990. The MOBI is similar to the MIRF in concept. That is, like the MIRF, the MOBI utilized off-the-shelf medical devices which are attached to the housing thereof so as to be transportable therewith, thus eliminating disruptions in the medical care provided thereby during transport.

Further examples of such contemporary life support systems include those disclosed in U.S. Pat. Nos. 4,584,989; 4,352,991; 4,691,397; 3,304,116; and 3,341,246.

U.S. Pat. No. 4,584,989 discloses a life support litter bed adapted to accommodate patients in intensive or cardiac care units in hospitals. The life support litter bed is broadly adapted for electrical medical devices, medical supplies and features an undercarriage including a support structural, wheels, a patient housing with a mattress, an electrical power source and supports for mounting the medical equipment.

U.S. Pat. No. 4,352,991 teaches a life support system adapted for field use in a vehicle with available power and includes electrically operable life support units, means for supporting the life support units, a patient litter, and a DC power source adapted for battery or remote power source.

U.S. Pat. No. 4,691,397 teaches a device for carrying the life supporting devices of a bedridden patient including a table like means for supporting the devices, an IV holder, wheeled transport means and a hospital bed footboard securing means.

U.S. Pat. No. 3,341,246 teaches a hospital litter adapted broadly with a litter structure having telescopic post elements and other means for manipulating the patient to various positions.

It is desirable for such transportable life support systems to be configured to accept a stretcher or litter. This litter compatibility allows a patient who has been brought to the transportable life support system on a litter to be placed upon the transportable life support system by merely placing the litter thereupon. As those skilled in the art will appreciate, it is extremely undesirable to move patients more than absolutely necessary. This restriction is particularly true with trauma or accident patients wherein the exact nature and extent of their injury is not known. Thus, it would be undesirable to be forced to set the litter next to a transportable life support system and then to have to move the patient from the litter to the transportable life support system by picking the patient up or rolling the patient over. Such movement of the patient undesirably exposes the patient to additional risk of injury or aggravation of an existing injury.

Thus, it is preferable to merely attach the litter upon which the patient is disposed to a transportable life support system. Such attachment of a litter to a transportable life support system necessitates the use of some type of latch or lock down for positively assuring attachment of the litter to the transportable life support system and also for facilitating quick release of litter from a transportable life support system when the patient arrives at a medical facility.

Thus, as it is desirable to facilitate attachment of the litter to the transportable life support system so as to prevent undesirable movement of the patient, it is likewise desirable to facilitate quick release of the litter from the transportable life support system so as to facilitate rapid movement of the patient away therefrom. Movement of the patient away from the transportable life support system typically occurs at a medical facility, where the patient may be moved from the transportable life support system to an operating table, for example. For the above mentioned reasons, it is similarly undesirable to pick up or roll the patient in order to accomplish such movement. Thus, it is preferable to pick up the litter, thus separating the litter from the transportable life support system, and to move the litter and patient together to the new location.

As those skilled in the art will appreciate, releasing the litter from the transportable life support system must be accomplished as quickly as possible, so that prompt medical attention may be provided to the patient. It is extremely undesirable to require that a procedure taking a substantial length of time be performed so as to effect release of the litter from the transportable life support system. Thus, the litter must be released from the transportable life support system as quickly as possible. This release is particularly important in situations where lifesaving medical attention must be provided to the patient as quickly as possible.

In view of the foregoing, it is desirable to provide means for simply, quickly, and reliably attaching a litter to a transportable life support system, wherein the litter may also be easily and quickly removed therefrom.

SUMMARY OF THE INVENTION

The present invention specifically addresses and alleviates the above mentioned deficiencies associated with the prior art. More particularly, the present invention comprises an automatic mechanical lock down for releasably attaching a litter to a transportable life support system. The mechanical lock down comprises a base having a recess formed therein. The recess is sized so as to receive a pole of a litter. A generally arcuate latch is pivotally attached to the base such that the latch has open and closed positions with respect to the recess and such that the latch is automatically pushed from the closed position thereof to the open position thereof when a litter pole is moved toward the recess of the base and such that the latch remains in the closed position thereof when a litter pole disposed within the recess is abutted against the latch.

A spring is attached to the base and the latch so as to move the latch back to the closed position thereof after the litter pole has been placed in the recess.

The automatic mechanical lock down is preferably configured such that a vertical axis of a point about which the latch pivot is offset or spaced apart from a vertical axis of a strike point of the latch. As used herein, the term strike point refers to that portion of the upper surface of the latch which contacts the litter pole when the litter pole is abutted against the latch during the process of attaching the litter to the transportable life support system. This offset causes the latch to push from the closed position to the open position due only to the downward pressure of the litter pole at the strike point.

According to the preferred embodiment of the present invention, the latch further comprises a knurled surface formed on an upper surface thereof so as to facilitate opening of the latch such that the litter pole can easily be removed therefrom. As used herein, the term knurl is defined to include any grooved or roughened condition of a surface which enhances a user's grip thereon. The knurled surface is formed proximate the strike point, but the strike point itself is preferably not knurled. The knurled surface formed on the latch thus facilitates opening of the latch with a thumb of a hand which is grasping the litter pole. That is, according to the present invention, the litter pole does not have to be let go of in order to release the litter pole from the mechanical lock down, as discussed in detail below.

The latch is configured so as to substantially close the recess when a litter pole is disposed within the recess such that the latch prevents the litter pole from being removed from the recess when the litter pole is moved toward the latch without first moving the latch to the open position thereof. This feature prevents the litter from undesirably and unintentionally being separated from the transportable life support system, particularly during handling and/or transport thereof. Thus, according to the present invention, rough handling, jostling, bouncing, etc. of the transportable life support system will not cause the litter poles to accidently separate from the mechanical lock downs.

More particularly, the latch is configured such that the strike point of a litter pole against an innersurface thereof, after the litter pole has been captured thereby, tends to maintain the latch in the closed position thereof, rather than tending to force the latch to open. Thus, the strike point of the litter pole against the inner surface of the latch occurs at a curved portion of the latch which is configured so as to capture and hold the litter pole when the latch is closed. The pivot pin of the latch and the curved inner surface thereof are configured such that upward pressure against the inner surface of the latch does not cause the latch to move from the closed position to the open position thereof. That is, urging the litter pole upwardly against the closed latch, as occurs when lifting the litter and carrying the self contained life support system, tends to maintain the latch in the closed position thereof. Thus, when lifting, carrying, and/or transporting the victim, the latches remain securely closed such that the litter does not inadvertently separate from the transportable life support system. The litter remains attached to the transportable life support system whether the litter and transportable life support system are being supported by the handles of the litter or the transportable life support system is resting upon a surface. Of course, when the litter and the transportable life support system is being suspended, as when being hand-carried or transported via a vehicle having litter holders. The entire weight of the litter, the transportable life support system, and the patient is being supported by the four latches of the transportable life support system, which has been specifically designed so as to prevent inadvertent opening thereof.

In use, a litter pole is abutted downwardly against the generally arcuate latch so as to contact the strike point of the latch and cause the latch to move against the urging of the spring from the closed position to the open position thereof, thus allowing the litter pole to enter the recess formed in the base. Then the latch moves from the open position to the closed position thereof via the urging of the spring. Thus, the latch captures the litter pole within the recess of the base in a manner which facilitates easy intentional releasing thereof and which inhibits accidental release thereof.

The litter is released from the transportable life support system by using the thumb of a hand which is grasping the litter pole so as to move the latch from the closed position to the open position thereof. In this manner, two people, one disposed at each end of the litter and each person grasping both litter poles, may utilize the thumbs of their hands to open the mechanical lock down (by moving the latches from the closed position to the open position thereof with their thumbs) without having to release their grip on the litter poles, so that they may immediately pick up the litter and move the patient away from the transportable life support system.

Thus, according to the present invention, means is provided for rapidly, easily, and reliably attaching a litter to a transportable life support system and also for quickly and easily releasing the litter from the transportable life support system. Such quick attachment and release of the litter to and from the transportable life support system mitigates the need to move the patient without using the litter, thus mitigating the risk of injuring the patient or aggravating an existing injury.

DETAILED DESCRIPTION OF THE PREFERRED INVENTION

The detailed description set forth below in connection with the appended drawings is intended as a description of the presently preferred embodiment of the invention, and is not intended to represent the only form in which the present invention may be constructed or utilized. The description sets forth the functions and the sequence of steps for constructing and operating the invention in connection with the illustrated embodiment. It is to be understood, however, that the same or equivalent functions may be accomplished by different embodiments that are also to be encompassed within the spirit and scope of the invention.

The mechanical lock down of the present invention is illustrated in FIGS. 1 through 5 which depict a presently preferred embodiment thereof.

Figure 1:
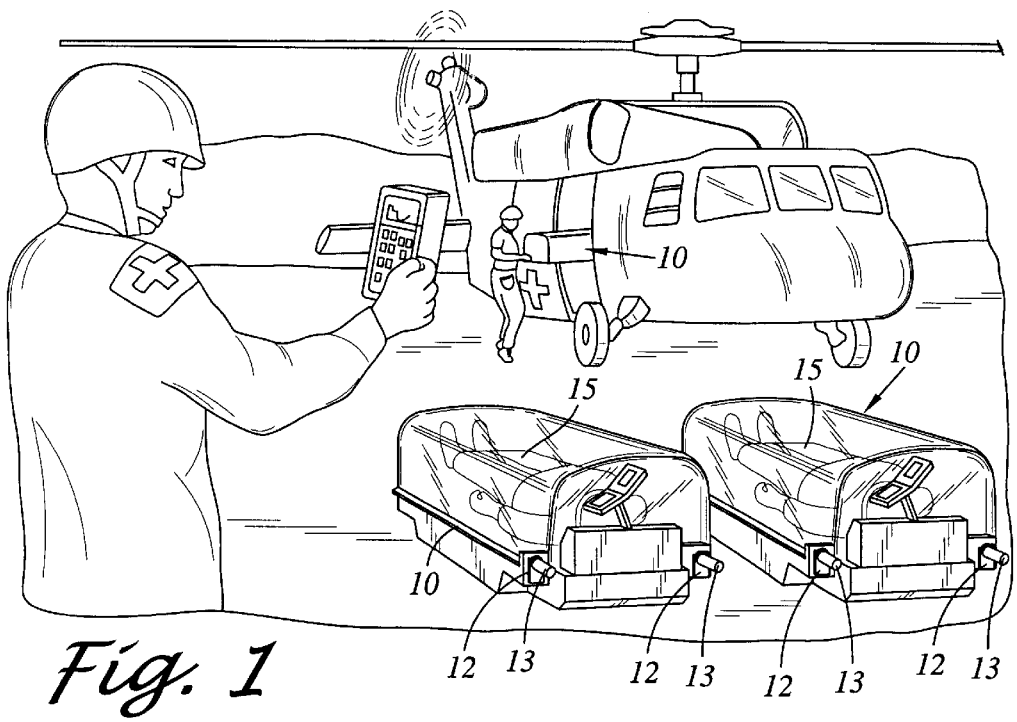
FIG. 1 is a perspective view showing two transportable life support systems having mechanical lock downs according to the present invention for attaching litters thereto.
Figure 2:
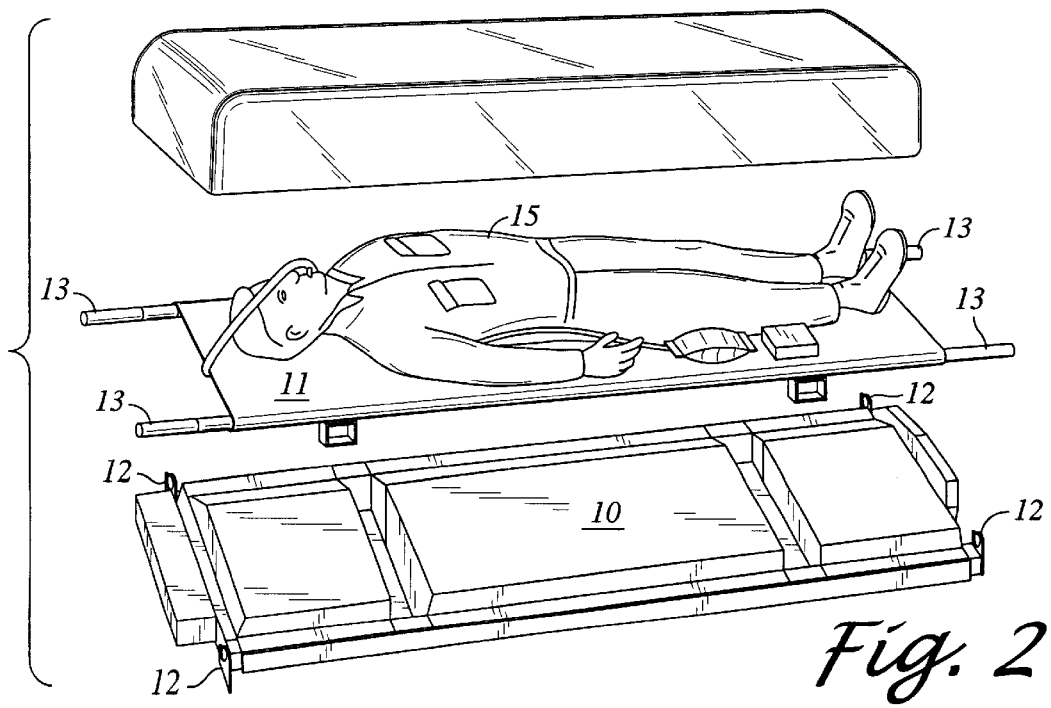
FIG. 2 is an exploded perspective view showing a transportable life support system of FIG. 1 having the litter separated away therefrom.

Referring now to FIGS. 1 and 2, transportable life support systems 10, which typically comprise a plurality of medical monitoring and medical treatment devices for facilitating the transport of injured or critically ill patients, comprises four mechanical lock downs 12, one proximate each corner of the transportable life support system 10, for attaching the litter poles 13 of the litter 11, upon which the patient is disposed, to the transportable life support system 10 in a manner which facilitates secure, reliable attachment as well as quick and easy release thereof. Thus, according to the present invention a litter 11 can be quickly placed upon a transportable life support system 10 with the mechanical lock downs 12 automatically releasably securing the litter 11 to the transportable life support system 10. The mechanical lock downs 12 may subsequently be released rapidly without releasing a grip upon the litter poles 13, so as to facilitate quick release of the patient 15 and litter 11 from the transportable life support system 10 when necessary.

Figure 3:
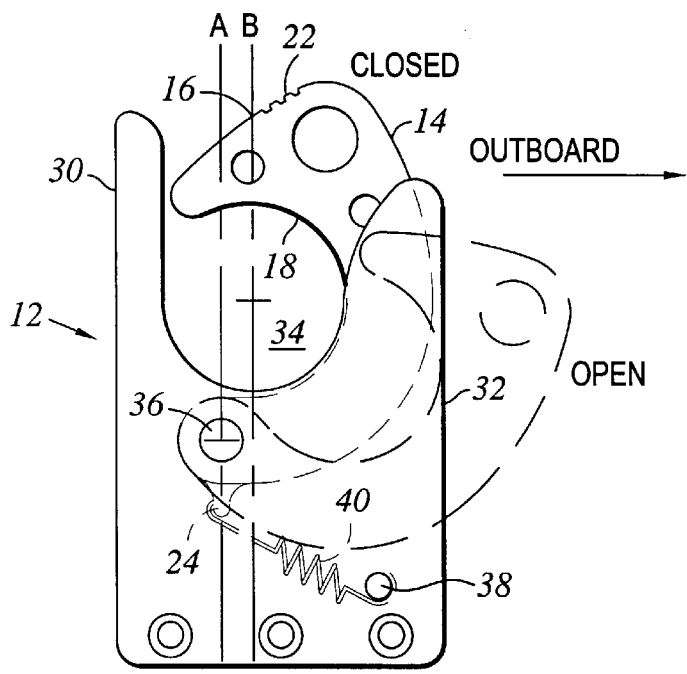
FIG. 3 is a front view of an automatic mechanical lock down according to the present invention.
Figure 4:
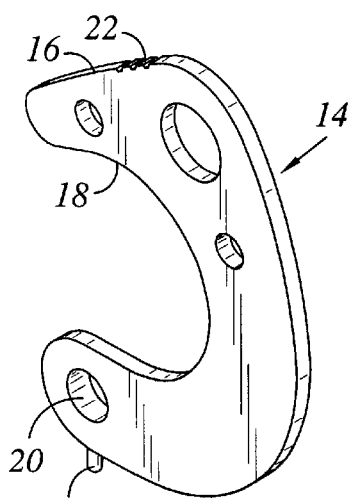
FIG. 4 is a perspective view of the latch of FIG. 3.
Figure 5:
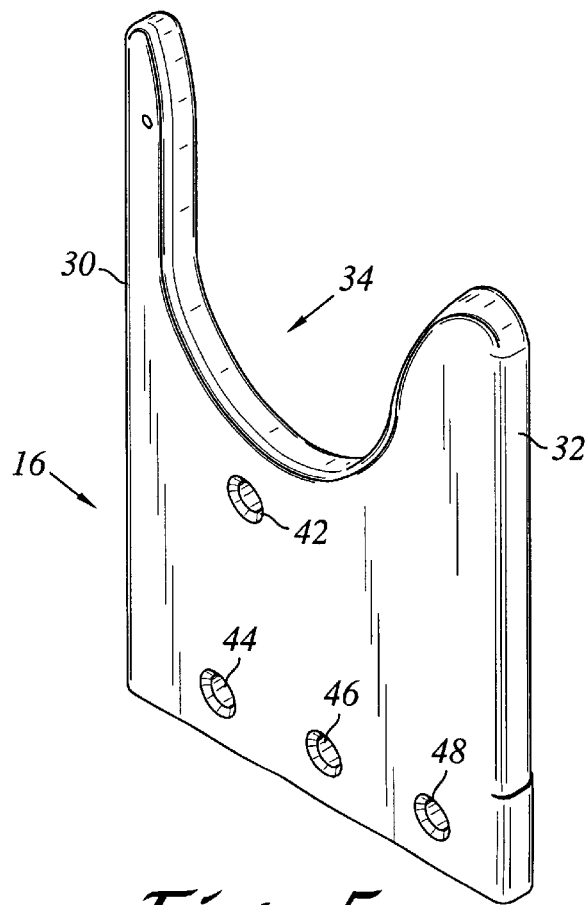
FIG. 5 is a perspective view of the base of FIG. 3.

Referring now to FIGS. 3–5, each mechanical lock down 12 generally comprises a latch 14 and a base 16. The base 16 is attached to the transportable life support system 10, typically via fasteners such as bolts or screws. Those skilled in the art will appreciate that various other means, such as welding, are likewise suitable for attaching the base 16 of each lock down 12 to the transportable life support system 10. The latch 14 is pivotally attached to the base 16 via pivot pin 36 which passes through aperture 20 of the latch 14 and aperture 42 of the base 16.

The base 16 may comprise either a single member having the latch 14 disposed on one side thereof as shown in FIG. 3, or alternatively may comprise two members which may either be identical to or different from one another and which sandwich the latch 14 therebetween. In this instance the pivot pin 36 preferably extends through both base members.

With particular reference to FIG. 4, each latch 14 comprises a strike area 16 which is generally smooth and unknurled. The strike area 16 is that area along the upper surface of the latch 14 where a pole 13 of a litter 11 contacts that latch 14 as the litter 11 is laid upon the transportable life support system 10. When the pole 13 contacts that strike surface 16 of the latch 14, it causes the latch 14 to pivot and move aside, so as to allow the litter pole to enter the locking cavity and effect locking of the litter 11 to the transportable life support system, i.e., locking of each pole 13 of the litter 11 to its respective mechanical tie down 12, as discussed in detail below.

According to the preferred embodiment of the present invention, the knurl 22 is formed along the upper surface latch 14 in a position which facilitates movement of the latch 14 from the closed position to the open position thereof via a user's thumb while the user maintains his grip upon a litter pole 13. The lower surface 18 of the latch 14 is that surface which a litter pole 13 abuts when the litter pole 13 is moved upwardly without first opening the latch 14. The mechanical lock down 12 of the present invention is typically configured so as to prevent inadvertent opening thereof when the transportable life support system 10 is carried and/or when the poles 13 are jostled or bounced about. Thus, the mechanical lock down 12 of the present invention provides a reliable means for securing the transportable life support system 10 to the litter 11.

Protrusion 24, preferably having a bore formed therethrough, facilitates attachment of spring 40 to the lower end of the latch 14 so as to bias the latch 14 in the closed position thereof. Spring 40 preferably attached to protrusion 24 by inserting one hooked end of spring 40 into the bore formed in the protrusion 24. The opposite end of spring 40 is preferably hooked around pin 38 of base 16. Those skilled in the art will appreciate that various other means for biasing the latch 14 in the closed position thereof are likewise suitable.

With particular reference to FIG. 5, the base generally comprises first 30 and second 32 upright members which define recess 34 into which the litter pole 13 is placed. The base 16 preferably further comprises aperture 42 through which pivot pin 36 extends for facilitating pivoting of latch 14. According to the preferred embodiment of the present invention, apertures 44, 46, and 48 facilitate attachment of the base 16 to the transportable life support system 10 via bolts, screws, or other fasteners, as desired. The lowermost end of spring 40 is preferably hooked about a pin, screw, bolt, or other fastener which passes through aperture 48.

Having discussed the structure of the mechanical lockdown of the present invention in detail, it may be beneficial to describe the operation thereof. A litter 11, which may or may not have a patient 15 disposed thereon is attached to a transportable life support system 10 by lowering the litter 11 onto the transportable life support system 10 in a manner which causes the poles 13 of the litter 11 to abut the contact surface 16 of each latch 14 and thus push each latch 14 aside, i.e., from the closed position to the open position thereof. By moving each latch 14 from the closed position to the open position thereof, the poles 13 are free to move downwardly into the recesses 34 of each mechanical lockdown 12.

Because the vertical axis A of the pivot pin 36 is offset with respect to the vertical axis B of the strike point 16, downward movement of a litter pole 13 causes the latch 14 to move from the closed position to the open position thereof (to rotate clockwise as shown in FIG. 3). Those skilled in the art will appreciate that such offset provides leverage which allows the downward movement of the litter pole 13 to effect rotation of the latch 14 which causes the latch 14 to move from the closed position to the open position thereof.

After the litter pole 13 is disposed within the recess 34 of the mechanical lockdown 12, then the latch 14 is urged back into to closed position thereof via spring 40 which maintains a bias upon the latch 14 so as to maintain the latch 14 in the closed position thereof during rough handling and transport of the life support system 10 having the litter 11 and patient 15 disposed thereon. Thus, according to the present invention, secure attachment of the litter 11 to the transportable life support 10 is provided.

Thus, when the transportable life support system 10 is carried via litter poles 13, the litter poles 13 abut lower surface 18 of each latch 14. However, each latch 14 is configured such that abutment of the litter poles 13 against the lower surface 18 thereof does not effect movement of the latch 14 from the closed position to the open position thereof, such that secure attachment of the litter 11 to the transportable life support system 10 is maintained. The latch 14 is configured so as to maintain such secure attachment by extending the generally arcuate length thereof sufficiently and by shaping the lower surface 18 such that upward movement of the litter poles 13 does not effect rotation of the latch 14 from the closed position to the open position thereof. Rather, when the pole 13 is lifted, the latch 14 hooks around it.

When it is desired to remove the litter 11 from the transportable life support system 10, then the transportable life support system 10 is rested upon a surface; and while maintaining their grip upon the litter poles 13, the persons carrying the litter 11 simply use their thumbs to rotate the latches 14 from the closed position to the open position thereof. That is, each of the two litter carriers maintains his grip upon one litter pole 13 with the fingers of each hand while using the extended thumbs of each hand to rotate the latches 14 from the closed position to the open position thereof. This task is accomplished by having the users thumbs contact the knurled surface 22 of each latch 14 and then by urging each latch 14 toward the open position thereof. The knurled surface 22 of each latch 14 provides more reliable engagement of each litter carrier's thumb with the latch 14. Thus, it is not necessary for the litter carriers to let go of the poles 13 in order to release the litter 11 from the transportable life support system 10.

Thus, according to the present invention, a litter 11 may be quickly attached to a transportable life support system by merely lowering the litter 11 onto the transportable life support system 10 and may be detached quickly therefrom by simply having each litter carrier use his thumb to move each latch 14 from the closed position to the open position thereof without releasing his grip upon the litter poles 13.

As those skilled in the art will appreciate, such quick and easy attachment and release of a litter 11 from the transportable life support system 10 is extremely important in life threatening situations wherein the patient requires immediate medical attention. During a medical emergency, it is extremely important that medical attention be provided as quickly as possible. For example, if the patient is bleeding, suffering from a heart attack, or a stroke, or not breathing, then it is very likely that a delay of even a few seconds may make the difference between life and death.

It is understood that the exemplary automatic mechanical lock down described herein and shown in the drawings represents only a presently preferred embodiment of the invention. Indeed, various modifications and additions may be made to such embodiment without departing from the spirit and scope of the invention. For example, the base may comprise various different configurations from that shown and described. It is necessary that only a recess 34, configured to receive a litter pole 13 be provided. Furthermore, although certain aspects of the latch 14 are crucial, such as the configuration thereof so as to facilitate easy attachment and release of the litter poles 13. Thus, the latch may be readily modified or changed in shape and yet maintain the novel characteristics described above and function in a similar manner. Thus, these and other modifications and additions may be obvious to those skilled in the art may be implemented to adapt the present invention for use in a variety of different applications.

What is claimed is:

1. A method of releasably attaching a mechanical lock down to a litter pole comprising the steps:

a) providing a mechanical lock down defined by a generally arcuate latch, a base with a recess, and a spring, the latch being movably attached to the base with the recess and operative to transition between a closed position wherein the latch extends over the recess and a second open configuration wherein said latch is extensible from the recess, the spring being operative to bias the latch to the closed configuration;

b) abutting the litter pole against the generally arcuate latch base to move the latch against the biased force generated by the spring from the closed configuration to the open configuration;

c) positioning the litter pole onto the recess;

d) moving the latch from the open position to the closed position via the biased force generated by the spring, the latch and the recess substantially engaging the litter pole; and e) lifting the litter pole for engagement against the latch, the latch being maintainable in the closed position to support the upward force exerted by the litter pole.

2. The method of claim 1 wherein subsequent step b) comprises pushing the pivotally attached latch with a thumb of a hand against the biased force generated by the spring from a closed position.

* * * * *